United States Patent [19]

Knifton

[11] Patent Number: 4,734,518

[45] Date of Patent: Mar. 29, 1988

[54] PROCESS FOR COSYNTHESIS OF ETHYLENE GLYCOL AND DIMETHYL CARBONATE

[75] Inventor: John F. Knifton, Austin, Tex.

[73] Assignee: Texaco Inc., White Plains, N.Y.

[21] Appl. No.: 2,463

[22] Filed: Jan. 12, 1987

[51] Int. Cl.$^4$ ............................................. C07C 67/02
[52] U.S. Cl. ................................... 558/277; 568/858; 502/168; 502/150
[58] Field of Search ...................... 558/277; 568/858; 502/168, 150

[56] References Cited

U.S. PATENT DOCUMENTS

| | | | |
|---|---|---|---|
| 3,642,858 | 2/1972 | Frevel et al. | 558/277 |
| 3,803,201 | 4/1974 | Gilpin et al. | 558/277 |
| 4,062,884 | 12/1977 | Romano et al. | 558/277 |
| 4,181,676 | 1/1980 | Buysch et al. | 558/277 |
| 4,349,486 | 9/1982 | Brunelle et al. | 558/277 |
| 4,559,180 | 12/1985 | Green | 558/277 |

FOREIGN PATENT DOCUMENTS 2615665 10/1975 Fed. Rep. of Germany ...... 558/277

*Primary Examiner*—Michael L. Shippen
*Assistant Examiner*—Bruce D. Gray
*Attorney, Agent, or Firm*—Jack H. Park; Kenneth R. Priem; Cynthia L. Kendrick

[57] ABSTRACT

A process is disclosed for the cosynthesis of ethylene glycol and dimethyl carbonate by reacting methanol and ethylene carbonate in the presence of a homogeneous catalyst from the group consisting of soluble miscible tertiary phosphines arsines, and stibines and soluble, miscible bivalent sulphur and selenium compounds.

7 Claims, No Drawings

PROCESS FOR COSYNTHESIS OF ETHYLENE GLYCOL AND DIMETHYL CARBONATE

This invention concerns a process for cosynthesis of ethylene glycol and dimethyl carbonate by the transesterification reaction of ethylene carbonate and methanol in the presence of a homogeneous Group VB or Group VIB catalyst selected from the group consisting of soluble, miscible tertiary phosphines, tertiary arsines, tertiary stibines, bivalent sulfur compounds and bivalent selenium compounds. In addition to the fact that substantially fewer moles of methanol are needed in the methanol-ethylene carbonate feedstock per mole of dimethyl carbonate produced, this invention is advantageous in that the use of certain tertiary phosphines are particularly effective as a catalyst type for dimethyl carbonate-ethylene glycol cosynthesis.

BACKGROUND OF THE INVENTION

Generally the prior art reports that the transesterification of aliphatic hydroxy compounds with carbonic acid, aliphatic diesters and aromatic diesters occurs readily in the presence of a basic catalyst and is a convenient method of synthesis of higher carbonates.

Several references deal with the transesterification of glycol carbonates using an aliphatic alcohol. Most demonstrate the use of methanol and ethylene carbonate.

In a process disclosed in U.S. Pat. No. 4,181,676 there is taught a method for preparation of dialkyl carbonate by contacting a glycol carbonate of a 1,2-diol, having 2 to 4 carbon atoms, with a selected group of alcohols at an elevated temperature in the presence of an alkali metal or alkali metal compound wherein the improvement comprises employing less than 0.01 percent by weight of alkali metal or alkali metal compound based on the weight of the reaction mixture.

It is known that alkyl carbonates of the type RO-COOR can be obtained from alcohols and cyclic carbonates corresponding to the above formula through a transesterification reaction in the presence of alkali alcoholates or hydrates; however, moderate amounts of inorganic compounds are produced by these reactions and must be removed by methods which may unfavorably affect the general economy of the process.

In U.S. Pat. No. 4,062,884 this problem was addressed and it was found that dialkyl carbonates can be prepared by reacting alcohols with cyclic carbonates in the presence of organic bases, which makes it unnecessary to remove inorganic compounds and allows the catalyst to be totally recovered by means of simple distillation. The preferred organic base is a tertiary aliphatic amine.

U.S. Pat. No. 3,642,858 discloses a process for producing carbonates having the formula

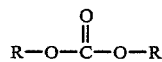

which comprises contacting an alkylene carbonate having the formula

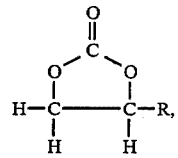

with a non-tertiary hydroxy-containing compound having the formula

while in the presence of a catalytic amount of an alkali metal or a derivative thereof. The process avoids the use of phosgene as a starting material and results in a clean reaction product involving fewer processing difficulties.

U.S. Pat. No. 4,349,486 teaches a monocarbonate transesterification process comprising contacting a beta-fluoroaliphatic carbonate, a compound selected from the class of monohydroxy aliphatic alcohols, monohydroxy phenols and ortho-positioned dihydroxy aromatic compounds in the presence of a base. This invention claims to greatly reduce undesirable side reactions and only small amounts of carbonic acid-aliphatic-aromatic mixed diester are associated with the isolated aromatic monocarbonate reaction.

The Gilpin and Emmons Patent, U.S. Pat. No. 3,803,201, discusses problems associated with the separation of the methanol, dimethyl carbonate azeotrope and teaches one solution, wherein dimethyl carbonate is isolated from the azeotrope by a combination of low temperature crystallization and fractional distillation.

In another article in the *J. Org. Chem.* 49(b) 1122–1125 (1984) Cella and Bacon discuss the results of their work. Among other things, they found that the alkylation of alkali metal bicarbonate and carbonate salts with alkyl halides in dipolar aprotic solvents and phase-transfer catalysts produces alkyl carbonates in good yields. The major limitation of this method is the failure of activated aryl halides or electronegatively substituted alkyl halides to produce carbonates due to the facility with which the intermediate alkoxy carbonate salts decompose.

Disadvantages of the methods discussed above include in many cases the fact that it is necessary to use a large amount of methanol feedstock relative to the amount of dimethyl carbonate produced. Also, in many cases, alkali metal halides are coproduced and these halides present disposal problems.

It would be a substantial advance in the art to devise an efficient catalyst for co-producing dimethyl carbonate and ethylene glycol, which was homogenous and did not necessitate difficult product-catalyst separations. The dimethyl carbonate produced by this novel process can be used as a gasoline extender.

SUMMARY OF THE INVENTION

This invention concerns a process for the cosynthesis of ethylene glycol and dimethyl carbonate from ethylene carbonate and methanol by reacting ethylene carbonate and methanol in the presence of a homogeneous Group VB or Group VIB catalyst selected from the group consisting of tertiary phosphines, tertiary arsines, tertiary stibines, bivalent sulphur and selenium compounds, at a temperature of from 20° C. to 200° C. and an operative pressure of zero to 5000 psig, until the desired products are formed.

A particular advantage of these systems over the prior art is the high selectivities to dimethyl carbonate (DMC) and ethylene glycol (EG)-basis the ethylene carbonate (EC) and methanol (MeOH) charged. These selectivities are illustrated in the accompanying Example I for the tri-n-butyphosphine catalyst and Example II for the triphenylphosphine catalyst precursor.

DETAILED DESCRIPTION OF THE INVENTION

In the narrower and more preferred practice of this invention dimethyl carbonate and ethylene glycol are prepared simultaneously by a transesterification process which comprises reacting ethylene carbonate and methanol in the presence of a homogeneous Group VB or Group VIB catalyst, at a temperature of between 50° C. and 150° C., and a pressure of at least 50 psig, until the desired products are formed.

Starting materials employed in the process are an aliphatic alcohol and a cyclic, aliphatic carbonate. Alcohols which work in the process of this invention include the aliphatic monohydric alcohols containing one to 12 carbon atoms, including methanol, ethanol and propanol. Methanol is the preferred alcohol.

Cyclic, aliphatic carbonates, such as ethylene carbonate and propylene carbonate will work as reactants. Alkylene carbonates which will work in the process of this invention include the carbonate derivatives of 1,2-diols containing two to 10 carbon atoms per molecule, including ethylene carbonate, 1,2-propylene carbonate and 1,2-butanediol carbonate. Ethylene carbonate is the preferred alkylene carbonate feedstock for this process. The preferred starting materials are illustrated in the accompanying examples. Recovery of the desired ethylene glycol and dimethyl carbonate can generally be carried out by distillation and crystallization.

More specifically, methanol and ethylene carbonate are pumped into a tubular reactor upflow at a flow rate of 0.1 to 100 liquid hourly space velocity (LHSV). The reactor temperature is held at between 20° and 200° C. and a back pressure of zero to 5000 psi is maintained throughout the experiment.

The homogeneous catalyst system suitable for the practice of this invention generally comprise a compound of Group VB or VIB. The compound can be in the form of a salt or complex. Particularly effective are tertiary phosphines, tertiary arsines, tertiary stibines, bivalent sulphur and bivalent selenium compounds.

The phosphine-containing catalyst compound comprises a soluble/miscible tertiary phosphine or a complex. Suitable tertiary phosphines contain one or more trivalent phosphorous atoms per molecule bonded to suitable alkyl, aryl, alkaryl, substituted alkyl, substituted aryl radicals, as well as alkoxy and aryloxy radicals, and mixtures thereof. Suitable alkyl radicals contain one to 20 carbons and may include methyl, ethyl, n-propyl, iso-propyl, n-butyl, tert-butyl as well as cyclic alkyl radicals such as the cyclohexyl radical, $C_6H_{11}$. Suitable aryl radicals may contain 6 to 20 carbon atoms and may include phenyl, o-tolyl, p-tolyl as well as substituted aryl radicals such as p-chlorophenyl and p-methoxyphenyl. Suitable alkoxy radicals may contain 1 to 20 carbon atoms and may include methoxy, ethoxy and butoxy radicals.

Said trivalent phosphorous atoms in the tertiary phosphine catalyst utilized in the practice of this invention may also be bonded to hydrogen, halogen and nitrogen, as well as to mixtures thereof of the radicals defined above.

Examples of suitable tertiary phosphine catalysts include tri-n-butylphosphine, triphenylphosphine, tri-n-butylphosphite, $P(OBu)_3$, tri-c-hexylphosphine, diphenylmethylphosphine, phenyldimethylphosphine diphenylphosphine, $PPh_2H$, diphenylchlorophosphine, $PPh_2Cl$, hexamethylphosphorous triamide, $(Me_2N)_3P$, Di-n-butylchlorophosphine, butyldiphenylphosphine, diethylphosphine, tri-n-hexylphosphine, triethylphosphine, triphenylphosphite, tri-p-tolylphosphine, tri-o-tolylphosphine, tri(m-chlorophenyl)phosphine, tri(p-methoxyphenyl)phosphine, and tribenzylphosphine.

Also effective are tertiary phosphine catalysts containing two or more trivalent phosphorous atoms per molecule. Here suitable examples include 1,2-bis(diphenylphosphine)ethane, 1,3-bis(diphenylphosphino)propane, $Ph_2P(CH_2)_3PPh_2$, 1,5-bis(diphenylphosphino)pentane and 1,2-bis(diethylphosphino)ethane.

The preferred tertiary phosphine catalysts include tri-n-butylphosphine, triphenylphosphine, diphenylmethylphosphine, diphenylphosphine, and 1,3-bis(diphenylphosphino)propane. Each of these tertiary phosphines are dissolved in the ethylene carbonate-methanol feed mix in the practice of this invention.

The tertiary arsine catalyst compound may likewise contain one or more trivalent arsinic atoms bonded to suitable alkyl, aryl, alkaryl, substituted alkyl, substituted aryl, alkoxy and aryloxy radicals, as well as mixtures thereof. The trivalent arsenic atoms may also be bonded to hydrogen or halogen.

Examples of suitable tertiary arsine catalysts include triphenylarsine, 1,2-bis(diphenylarsino)ethane, trimethylarsine and tri-n-butylarsine. The preferred arsine compound is 1,2-bis(diphenylarsino)ethane.

Examples of suitable tertiary stibine catalysts may likewise contain one or more tertiary antimony atoms bonded to the radicals listed SUPRA. Examples include triphenylantimony, antimony(III) ethoxide, and antimony(III) methoxide.

Suitable sulphur-containing catalyst precursors for EC/MeOH transesterification include soluble, miscible, bivalent compounds containing one or more sulphur atoms per molecule bonded to suitable alkyl, aryl, alkaryl, substituted alkyl, and substituted aryl radicals. The bivalent sulphur atoms may also be bonded to hydrogen or to other sulphur atoms.

Examples of suitable divalent sulphur catalysts include diphenylsulfide, phenyl disulfide and ethyl sulfide.

Suitable selenium-containing catalyst precursors include bivalent compounds containing one or more selenium atoms per molecule bonded to the radicals listed SUPRA.

Examples of suitable selenium compounds include diphenyl selenide and phenyl diselenide.

For ethylene carbonate-methanol transesterifications run in the upflow mode in a tubular reactor at 100°–150° C., 100 psi, 0.5 LHSV the order of activity for the tertiary phosphine catalysts appear to be:

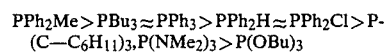

The effectiveness of these catalyst precursors is illustrated in the accompanying examples, shown in Table I.

Said Group VB and VIB catalysts may be solubilized in the ethylene carbonate-methanol liquid feed mixtures at concentrations of from 0.001 to 50 wt % in the practice of this invention.

Typically, the concentration of tertiary phosphine in the EC-MeOH feed is from 0.1 to 10 wt % of the sample. In some cases it may be necessary to filter said solutions, prior to use for transesterification to dimethyl carbonate-ethylene glycol, due to the precipitation of insoluble solids.

The reaction can be represented by the following equation:

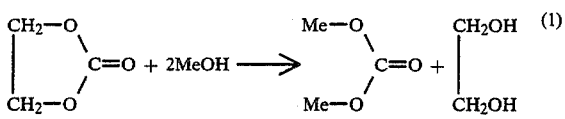

During the cosynthesis of ethylene glycol and dimethyl carbonate by the reaction of ethylene carbonate with methanol (Eq. 1), a large excess of methanol is normally employed in the prior art. Usually the initial molar ratio of methanol to ethylene carbonate is in the range of 5 or greater, and preferably at least 10. This preferred ratio range is illustrated by U.S. Pat. No. 3,803,201 (1974). In the practice of this invention, by contrast, the initial weight ratio of ethylene carbonate to methanol is preferably 1:1 to 1:5. Such a range of weight ratios is illustrated by the accompanying examples.

Potential advantages to operating at this ethylene carbonate-to-methanol weight ratio include:
(a) More efficient transesterification.
(b) Lower levels of methanol required to be recycled after the transesterification step.

Ethylene glycol-dimethyl carbonate synthesis using the homogeneous catalyst described SUPRA can be conducted at reaction temperatures in the range from 20° to 200° C. The preferred operating temperature range is 50°–150° C.

The reaction can be conducted under atmospheric pressure. A pressure reactor is nevertheless required in the case of low-boiling point components if the reaction is to be carried out in the upper temperature range and in the liquid phase. The pressure is not critical. In general the reaction is allowed to proceed under the autogenous pressure of the reactants. However, the reaction can also be carried out under elevated pressure, for example, under an inert atmosphere. A pressure of zero to 5000 psig is appropriate here. An operating pressure of greater than 50 psig is suitable and the preferred pressure is in the range of 50 to 150 psi.

The residence time for the ethylene carbonate and methanol reactants in the tubular reactor may vary over a wide range according to the temperature of reaction, the molar ratios of carbonate/alcohol feedstocks, etc. Using the homogeneous catalysts of this invention, the necessary residence time in the reactor may range from 0.01 hours to 10 hours, although it may be extended beyond 10 hours without danger of additional by-products being formed. The preferred residence time is in the range of 0.1 to 5 hours.

The desired products of this process according to the invention are ethylene glycol and dimethyl carbonate. By-products include diethylene glycol, unreacted ethylene carbonate and methanol, ethylene glycol monomethyl ether, 1,1-dimethoxyethane, 1,2-dimethoxyethane, methyl 1,3-dioxolane and dimethyl ether.

Products have been identified in this work by gas chromatography (gc), NMR, IR and gc-IR or a combination of these techniques. Phosphine, arsine and sulphur analyses were by atomic absorption (AA). All liquid product analyses have, for the most part, been by gc; all temperatures are in degrees centigrade and all pressures in pounds per square inch gauge.

The following examples illustrate the novel process of this invention. The examples are only for illustrating the invention and are not considered to be limiting:

EXAMPLE I

Example I illustrates a typical dimethyl carbonate/ethylene glycol cogeneration using a catalyst a solution of tri-n-butylphosphine in the ethylene carbonate-methanol feed mix. 100.0 g of tri-n-butylphosphine was added to a 2 kg. mixture of ethylene carbonate (EC) and methanol (typical composition 64.9% MeOH, 34.2% EC). The mixture was stirred to dissolve the phosphine, and the clear, water-white, liquid feed pumped to a 50 cc capacity, tubular reactor upflow, at a rate of 25 cc/hr. The reactor temperature was held at 100° C., and a back pressure of 100 psi was maintained throughout the experiment. After feeding the ethylene carbonate-methanol mix for several hours (3–8), the liquid effluent was sampled at regular time intervals and analyzed by gas-liquid chromatography. Typically, this liquid effluent had the following composition:

18.0 wt % dimethyl carbonate (DMC)
11.0 wt % ethylene glycol (EG)
14.6 wt % ethylene carbonate (EC)
50.4 wt % methanol (MeOH)
0.2 wt % ethylene glycol monomethyl ether Estimated molar selectivity to $EG$, basis MeOH converted =

$$\frac{(11.0/62) \times 2}{(64.9 - 50.4)/32} \times 100 = 80\%$$

where $DMC\ FW = 90.0$; $EC\ FW = 88.0$;

$EG\ FW = 62.0$; $MeOH\ FW = 32.0$

EXAMPLES II–XIV

In Examples II through XIV various homogeneous Group VB and VIB catalysts are evaluated for EC/MeOH transesterification using the precursors of Example I. Conditions remain constant, the data are summarized in Table I.

It may be noted from Table I that various classes of Group VB and VIB catalysts are effective for the coproduction of dimethyl carbonate and ethylene glycol. These include:
(1) Tertiary phosphines such as triphenylphosphine, tri-c-hexylphosphine, hexamethylphosphorous triamide, diphenylchlorophosphine, diphenylmethylphosphine, diphenylphosphine and 1,3-bis(diphenylphosphino)propane.
(2) Tertiary phosphites such as tributylphosphite.
(3) Tertiary arsines such as 1,2-bis(diphenylarsino)ethane and triphenylarsine.
(4) Tertiary stibines such as triphenylantimony.
(5) Bivalent sulphur compounds such as diphenylsulfide.
(6) Bivalent selenium compounds such as diphenylselenide.

TABLE I

DIMETHYL CARBONATE/ETHYLENE GLYCOL COGENERATION[a]

| Example | Catalyst | Conc. Wt. % | Temp. °C. | DMC | EG | EC | MeOH | Sample No. |
|---|---|---|---|---|---|---|---|---|
| I | PBu₃ | 5.0 | 100 | 18.0 | 11.0 | 14.6 | 50.4 | −6 |
| | | | 130 | 17.4 | 11.2 | 15.6 | 50.7 | −12 |
| | | | 150 | 16.3 | 9.8 | 18.2 | 51.7 | −15 |
| II | PPh₃[b] | 4.1 | 130 | 16.3 | 10.1 | 18.2 | 54.2 | −1 |
| | | | 150 | 17.9 | 11.3 | 15.6 | 52.9 | −15 |
| III | P(OBu)₃ | 5.0 | 130 | 0.4 | 0.2 | 32.6 | 62.0 | −1 |
| | | | 150 | 0.2 | 0.3 | 36.2 | 55.9 | −15 |
| IV | P(c-C₆H₁₁)₃[b] | 0.8 | 100 | 2.3 | 1.7 | 34.4 | 59.8 | −13 |
| | | | 130 | 10.3 | 6.7 | 27.7 | 53.7 | −2 |
| V | AsPh₃ | 3.3 | 100 | — | 0.2 | 36.7 | 62.2 | −7 |
| | | | 130 | 1.2 | 0.9 | 35.0 | 61.6 | −9 |
| VI | SPh₂ | 2.9 | 100 | 0.2 | 0.4 | 35.4 | 61.9 | −5 |
| | | | 130 | 0.6 | 0.5 | 35.8 | 61.1 | −13 |
| VII | P(NMe₂)₃ | 4.8 | 100 | 2.1 | 1.5 | 29.0 | 56.6 | −4 |
| | | | 130 | 3.5 | 2.4 | 24.5 | 59.9 | −8 |
| | | | 25 | 1.6 | 1.5 | 30.0 | 55.6 | |
| VIII | PPh₂Cl[b] | 2.6 | 25 | 6.8 | 4.3 | 31.2 | 56.4 | |
| | | | 100 | 7.5 | 4.8 | 30.1 | 56.0 | −5 |
| IX | SbPh₃ | 2.5 | 130 | 0.5 | 0.5 | 35.0 | 62.9 | −4 |
| | | | 150 | 2.0 | 1.4 | 37.9 | 58.0 | −8 |
| X | Ph₂As(CH₂)₂AsPh₂[b] | 1.0 | 130 | 4.8 | 3.4 | 31.6 | 59.3 | −7 |
| | | | 150 | 1.7 | 1.3 | 36.1 | 60.3 | −8 |
| XI | PPh₂Me | 2.6 | 130 | 18.1 | 11.5 | 19.5 | 48.3 | −7 |
| | | | 150 | 19.1 | 12.0 | 19.6 | 46.2 | −13 |
| XII | PPh₂H | 2.4 | 130 | 5.9 | 3.8 | 32.2 | 56.1 | −4 |
| | | | 150 | 15.9 | 10.1 | 27.7 | 44.1 | −7 |
| XIII | SePh₂ | 2.0 | 130 | 5.1 | 3.3 | 32.0 | 58.2 | −6 |
| | | | 150 | 8.4 | 5.5 | 31.1 | 53.2 | −13 |
| XIV | Ph₂P(CH₂)₃PPh₂[b] | 0.4 | 130 | 8.8 | 5.7 | 30.9 | 53.7 | −6 |
| | | | 150 | 15.0 | 9.7 | 28.3 | 45.9 | −10 |

[a]Run in continuous, 50 cc capacity, tubular reactor, upflow, 100 psi pressure, 25 cc/hr, feed composition ca. 63% MeOH, 37% EC.
[b]Solution in EC/MeOH was filtered prior to use.

What is claimed is:

1. A process for cosynthesis of ethylene glycol and dimethyl carbonate which comprises reacting ethylene carbonate and methanol in the presence of a homogeneous catalyst selected from the group consisting of bivalent sulphur and bivalent selenium compounds at a temperature of 20° to 200° C. until the desired products are formed.

2. The process of claim 1 wherein the homogeneous catalyst is a bivalent sulfide from the group consisting of diphenylsulfide and phenyldisulfide.

3. The process of claim 1 wherein the homogeneous catalyst is a bivalent selenide from the group consisting of diphenylselenide and phenyl diselenide.

4. The process of claim 1 wherein the operating temperature is between 50° and 150° C.

5. The process of claim 1 wherein the operating pressure is between zero and 5000 psig.

6. The process of claim 1 wherein the weight ratio of methanol to ethylene carbonate is in the range of 1:1 to 5:1.

7. A process for cosynthesis of ethylene glycol and dimethyl carbonate by reacting ethylene carbonate and methanol containing a homogeneous catalyst dissolved therein from the group consisting of diphenylsulfide, phenyl disulfide, diphenylselenide and phenyl diselenide.

* * * * *